United States Patent [19]
Voss et al.

[11] Patent Number: 5,908,963
[45] Date of Patent: Jun. 1, 1999

[54] PREPARATION OF FUEL GRADE DIMETHYL ETHER

[75] Inventors: Bodil Voss, Virum; Finn Joensen, Hørsholm; John Bogild Hansen, Copenhagen Ø, all of Denmark

[73] Assignee: Holdor Topsoe A/S, Lyngby, Denmark

[21] Appl. No.: 08/894,066

[22] PCT Filed: Jan. 29, 1996

[86] PCT No.: PCT/DK96/00047

§ 371 Date: Dec. 12, 1997

§ 102(e) Date: Dec. 12, 1997

[87] PCT Pub. No.: WO96/23755

PCT Pub. Date: Aug. 8, 1996

[30] Foreign Application Priority Data

Feb. 3, 1995 [DK] Denmark ................................. 0120/95

[51] Int. Cl.$^6$ ............................. C07C 41/00; C07C 27/00
[52] U.S. Cl. ............................. 568/671; 568/698; 518/700
[58] Field of Search .............................. 518/700; 568/671, 568/698

[56] References Cited

U.S. PATENT DOCUMENTS 5,218,003  6/1993  Lewnard et al. ........................ 518/700

FOREIGN PATENT DOCUMENTS 0 409 086 A1  1/1991  European Pat. Off. .
4222655 A1   1/1994  Germany .

*Primary Examiner*—Paul J. Killos
*Assistant Examiner*—Jafar Parsa
*Attorney, Agent, or Firm*—Morgan, Lewis & Bockius LLP

[57] ABSTRACT

A process for the preparation of dimethyl ether. The process prepares fuel grade dimethyl ether from a hydrogen and carbon oxides synthesis gas.

4 Claims, 1 Drawing Sheet

PREPARATION OF FUEL GRADE DIMETHYL ETHER

This invention is directed to the preparation of dimethyl ether (DME). The invention concerns in particular a process for the production of fuel grade DME containing small amounts of methanol and water from a $H_2/CO/CO_2$ comprising synthesis gas.

Presently, DME is used in the industry for the manufacture of synthetic gasoline. Further industrial applications comprise the use of DME as aerosol propellant and more recently as intermediate in the production of acetic acid.

The major route in the production of DME on industrial scale comprises dehydration of methanol by use of a dehydration catalyst in a fixed bed reactor, and rectification of the product to recover a DME product with high purity as required by the aerosol industry.

From the literature, a number of alternative preparation methods are known including direct synthesis of DME from hydrogen and carbon oxides. Preparation of DME directly from $H_2/CO/CO_2$ synthesis gas in a fixed bed reactor of a combined methanol catalyst and dehydration catalyst is disclosed in DD 291,937, U.S. Pat. No. 5,254,596, EP 164,156, U.S. Pat. No. 4,417,000, U.S. Pat. No. 4,177,167, U.S. Pat. No. 4,375,424, GB 2,093,365, GB 2,097,382, U.S. Pat. No. 4,098,809, EP 409,086, GB 2,099,327, DE 3,220,547, DE 3,201,155, DE 3,118,620, DE 2,757,788, DE 2,362,944, DK 6031/87 and DK 2169/89.

The above prior art is mainly directed to preparation and utilization of catalyst compositions being active in preparation of methanol from synthesis gas and dehydration of methanol to DME by the following reaction scheme:

$$CO_2 + 3H_2 \leftrightarrows CH_3OH + H_2O \quad (1)$$
$$2CH_3OH \leftrightarrows CH_3-O-CH_3 + H_2O \quad (2)$$
$$CO + H_2O \leftrightarrows CO_2 + H_2 \quad (3)$$

Formation of methanol and DME is, by the above reaction scheme, limited by chemical equilibrium.

The effluent stream from the DME reactor is thus a mixed product stream of DME, methanol and water together with unreacted synthesis gas. A recycle stream of unreacted synthesis is separated from the product stream and recycled to the reactor. Because of a high partial pressure of DME in the product stream, part of produced DME will be removed together with the recycle stream.

To obtain reasonable conversion rates, it is necessary to remove DME from the recycle stream prior to recycling of the stream during direct DME synthesis. DME separation is thereby usually performed by a recycle gas wash.

DE 4,222,655 discloses a DME preparation process, wherein DME in a recycle gas stream from a high pressure separator is separated by washing the gas stream with methanol in a gas washing unit. The washed bottom stream from the washing unit contains DME and $CO_2$ and is later recombined with the product stream from the high pressure liquid separator. The combined product stream is subsequently washed in a second washing unit with methanol or water for the removal of $CO_2$ from the product stream The washed product stream containing DME and methanol in substantially equal amounts is finally subjected to a number of rectification stages to provide a DME product of high purity.

Recent investigations have shown that DME products containing up to 20% by mass methanol and up to 20% by mass water are efficient as fuel in compression ignition engines (Fleisch T., McCarthy C., Basu A., Udovich C., Charbonneau P., Slodowske W., Mikkelsen S. E., McCandless D., A New Clean Diesel Technology, Int. Congr. & Expos., Detroit, Mich., Feb. 27–Mar. 2, 1995).

As used herein above and in the following description, the term "fuel grade DME" refers to DME products with the above composition being useful as fuel in compression ignition engines and gas turbines.

By the known synthesis processes, the amount of methanol and water contained in DME raw product does not meet the specification of fuel grade DME. Excess of methanol in DME raw product produced represents a major drawback in the preparation of fuel grade DME by the known processes. Methanol has in the known processes either to be supplied from process external sources or excess of methanol removed and recycled to the process, which reduces the process efficiency towards the production of DME.

SUMMARY OF THE INVENTION

The main object of this invention is therefore to provide a process for the preparation of fuel grade DME without the disadvantages of the known processes for preparation of DME.

By the process of this invention, fuel grade dimethyl ether is prepared by reacting hydrogen and carbon oxides containing synthesis gas to a mixed process gas of dimethyl ether, methanol and water in one or more catalytic reactors in the presence of a catalyst having activity both in synthesis of methanol and in methanol dehydration;

cooling the mixed process gas to obtain a liquid process phase containing produced methanol, dimethyl ether and water and a gaseous process phase containing unconverted synthesis gas and a part of produced dimethyl ether, which process comprises further steps of separating the gaseous phase and liquid phase;

passing the liquid phase to a first distillation unit and distilling off a top product stream, containing dimethyl ether and methanol; and withdrawing a bottom stream containing methanol and water;

passing the bottom stream to a second distillation unit and distilling off a methanol containing stream;

introducing the methanol containing stream into a purge washing unit;

washing the gaseous process phase with methanol in the purge washing unit and withdrawing from the unit a washing stream of dimethyl ether and methanol;

converting a part of the methanol in the washing stream to dimethyl ether and water in a catalytic dehydration reactor by contact with a dehydration catalyst;

withdrawing and cooling from the dehydration reactor a product stream of dimethyl ether, water and unconverted methanol; and combining the top product stream from the first distillation unit with the cooled product stream from the dehydration reactor to obtain a combined product stream of fuel grade dimethyl ether.

DESCRIPTION OF THE INVENTION

Figure 1:
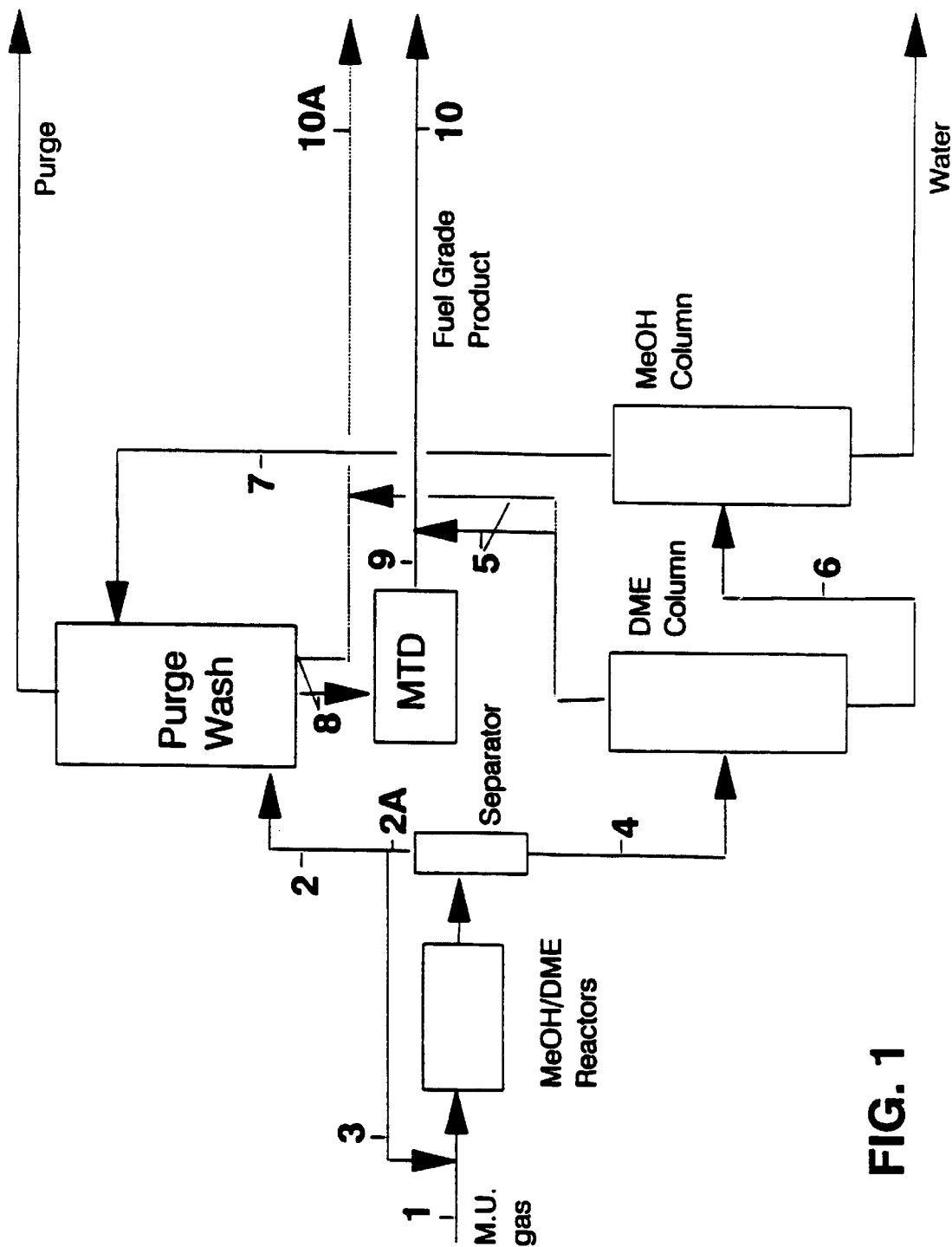
FIG. 1 depicts a flow sheet of a process for the preparation of fuel grade dimethyl ether according to the invention.

Preparation and conversion of synthesis gas to a DME containing process stream proceeds according to known methods in direct DME synthesis. Suitable catalysts for use in the synthesis gas conversion stage include conventional employed methanol catalysts such as copper, zinc and/or chromium based catalysts and methanol dehydration catalysts, which usually comprise alumina or alumina silicates as active compounds.

The catalysts may be loaded in the DME reactor as a physical mixture or as layered bed with alternating methanol synthesis and methanol dehydration catalyst particles. Physical mixtures of the catalysts result, however, in lower selectivity and formation of byproducts, mainly higher alcohols and hydrocarbons. Thus, it is preferred to employ a fixed bed of catalyst compositions comprising combined methanol formation, water gas shift and methanol dehydration activity. Such catalysts may be prepared by e.g. coprecipitation of the catalytic active materials according to known catalyst preparation methods as described in the literature, e.g. in the above mentioned patent publications, which by reference thereto are incorporated herein.

BRIEF DESCRIPTION OF THE DRAWINGS

Operation of the process will be apparent in more detail from the following description with reference to the drawings in which FIG. 1 represents a flow sheet of the process according to a specific embodiment of the invention. The flow sheet is simplified and various conventional units, such as heat exchanging and cooling units are not shown.

A synthesis gas stream 1 is reacted in a DME synthesis loop (MeOH/DME reactors), which may comprise a series of adiabatic reactors loaded with a combined methanol/DME catalyst and indirect cooling between the reactors or a cooled reactor for minor production capacities.

Fresh synthesis gas is mixed with a recycle gas stream 3 being separated from a process stream leaving the synthesis loop.

The synthesis gas is preheated in a feed effluent heat exchanger before introduction into the first reactor.

In the synthesis loop, the synthesis gas is converted to a mixed process gas of DME, methanol and water by the former reactions (1)–(3). The overall reaction is exothermic and heat of reaction is removed in intercoolers arranged between the reactors. The mixed process gas from the reactors in the loop is cooled and separated to a gaseous and liquid process phase stream 2 and 4, respectively.

The gaseous phase (2A) containing unconverted synthesis gas is divided into recycle gas stream 3 and purge gas stream 2. Due to the low condensability of DME in the mixed process gas, purge gas stream 2 further contains valuable amounts of DME, which are recovered in a purge washing unit by washing the purge stream with recycle methanol 7 from a methanol distillation column (MeOH column) in a final purification stage of the process.

Effluent stream 8 from the washing unit containing recovered DME is then passed to a dehydration reactor (MTD) with a fixed bed of a conventional methanol dehydration catalyst. By contact with the dehydration catalyst, methanol in the effluent stream is converted to DME by reaction (2) proceeding in the reactor and a dehydrated product stream 9 of DME, methanol and water is withdrawn from the reactor.

DME in the liquid process phase stream 4 is recovered by distillation of the stream in a DME distillation column. A DME top product stream 5 being withdrawn from the column is combined with dehydrated product stream 9 to a fuel grade DME product stream 10.

Methanol and water separated from the liquid process stream being withdrawn from the DME distillation column as bottom product stream 6 are subjected to further distillation in the methanol distillation column (MeOH column), from which a top product stream 7 of separated methanol is cycled to the purge washing unit as described above.

The actual composition of the final DME product stream 10 is by the process adjusted mainly by process parameters used in the DME synthesis loop.

Results obtained by engineering calculations on a process as described above are summarized in the Tables below. The stream numbers in the Tables correspond to the reference numbers shown in the FIG. 1.

Stream number 10A in Table 1 and 2 refers to a DME product stream obtained by a similar process with the exception of methanol washing stream 8 from the purge washing unit is not subjected to dehydration in dehydration reactor (MTD). The DME product stream 10A is thereby obtained by direct combination of effluent stream 8 with top product stream 5.

In the calculation, two different synthesis gas compositions (stream 1) were used resulting in fuel grade DME products with different methanol and water content as apparent from the Tables.

TABLE 1

| Stream No. | 1 | 2 | 3 | 4 | 5 | 6 | 7 | 8 | 9 | 10 | 10A |
|---|---|---|---|---|---|---|---|---|---|---|---|
| Flow Rate Rate [kmol/h] | 11020 | 1657 | 55099 | 3026 | 1195 | 1819 | 723 | 856 | 856 | 2026 | 2037 |
| Mass % | | | | | | | | | | | |
| $H_2$ | 13.05 | 12.80 | 12.80 | 0.01 | 0.00 | 0.00 | 0.00 | 0.05 | 0.05 | 0.02 | 0.02 |
| $H_2O$ | 0.03 | 0.07 | 0.07 | 20.87 | 0.01 | 46.96 | 1.30 | 1.09 | 18.82 | 6.57 | 0.39 |

TABLE 1-continued

| Stream No. | 1 | 2 | 3 | 4 | 5 | 6 | 7 | 8 | 9 | 10 | 10A |
|---|---|---|---|---|---|---|---|---|---|---|---|
| $N_2$ | 0.51 | 3.22 | 3.22 | 0.00 | 0.00 | 0.00 | 0.00 | 0.02 | 0.02 | 0.00 | 0.00 |
| CO | 82.47 | 21.20 | 21.20 | 0.04 | 0.01 | 0.00 | 0.00 | 0.17 | 0.17 | 0.00 | 0.01 |
| $CO_2$ | 1.70 | 20.83 | 20.83 | 0.64 | 0.88 | 0.00 | 0.00 | 1.82 | 1.82 | 1.20 | 1.20 |
| Ar | 0.46 | 2.88 | 2.88 | 0.00 | 0.00 | 0.00 | 0.00 | 0.01 | 0.01 | 0.00 | 0.00 |
| $CH_4$ | 1.78 | 11.02 | 11.02 | 0.03 | 0.01 | 0.00 | 0.00 | 0.14 | 0.14 | 0.06 | 0.06 |
| $CH_3OH$ | 0.0 | 0.47 | 0.47 | 27.70 | 7.56 | 53.04 | 98.70 | 79.49 | 16.46 | 10.66 | 32.72 |
| DMH | 0.0 | 27.52 | 27.52 | 50.71 | 91.53 | 0.00 | 0.00 | 17.21 | 62.51 | 81.49 | 65.60 |

TABLE 2

| Stream No. | 1 | 2 | 3 | 4 | 5 | 6 | 7 | 8 | 9 | 10 | 10A |
|---|---|---|---|---|---|---|---|---|---|---|---|
| Flow Rate [kmol/h] | 11020 | 2989 | 44080 | 3083 | 1003 | 2070 | 523 | 582 | 582 | 1568 | 1580 |
| Mass % | | | | | | | | | | | |
| $H_2$ | 14.8 | 26.2 | 26.2 | 0.0 | 0.0 | 0.0 | 0.0 | 0.0 | 0.0 | 0.0 | 0.0 |
| $H_2O$ | 0.0 | 0.00 | 0.0 | 31.6 | 0.0 | 63.9 | 2.6 | 2.3 | 21.1 | 6.3 | 0.7 |
| $N_2$ | 0.3 | 0.5 | 1.5 | 0.0 | 0.0 | 0.0 | 0.0 | 0.0 | 0.0 | 0.0 | 0.0 |
| CO | 49.7 | 7.6 | 7.6 | 0.0 | 0.0 | 0.0 | 0.0 | 0.0 | 0.0 | 0.0 | 0.0 |
| $CO_2$ | 30.1 | 24.3 | 24.3 | 0.8 | 1.1 | 0.0 | 0.0 | 2.2 | 2.2 | 1.3 | 1.3 |
| $CH_4$ | 5.0 | 28.9 | 28.9 | 0.0 | 0.0 | 0.0 | 0.0 | 0.1 | 0.1 | 0.0 | 0.0 |
| $CH_3OH$ | 0.0 | 0.1 | 0.1 | 21.0 | 6.4 | 36.1 | 97.4 | 84.3 | 17.4 | 9.7 | 29.5 |
| DMH | 0.0 | 11.4 | 11.4 | 46.4 | 92.5 | 0.0 | 0.0 | 11.1 | 59.2 | 82.7 | 68.4 |

As apparent from the results summarized in the Tables, the methanol content in DME products (stream 10A) obtained by a process without a dehydration reactor falls outside the concentration range, and the products are not useable in fuel grade DME products without further rectification.

EXAMPLE

This Example illustrates by reference to FIG. 1 preparation of fuel grade DME in pilot plant scale.

In a pilot plant comprising a feed gas preheater (not shown), a cooled MeOH/DME reactor and a subsequent product gas cooler (not shown), a gas/liquid separator and a recirculation compressor (not shown), 6.9 Nm³/h of a synthesis gas stream 1 is mixed with 26.5 Nm³/h of a recycle gas stream 3.

The mixed gas stream is then passed through the reactor and converted at a pressure of 42 bar and a temperature of 240–290° C. in presence of a catalyst as described above. The reacted gas stream is then cooled and separated into a liquid phase (2.8 kg/h) in stream 4 with a composition as shown in Table 3 below, and a gas stream 2A. Stream 2A was divided into recycle stream 3 and purge gas stream 2 (0.88 Nm³/h). Composition of the above streams as analyzed is summarized in Table 3 below.

TABLE 3

| Stream No | 1 | 3 | 4 | 2 | |
|---|---|---|---|---|---|
| Flow | 6.9 | 26.5 | 1.88 | 0.88 | Nm³/h |
| $H_2$ | 12.4 | 11.3 | 0.0 | 11.3 | Mass % |
| CO | 81.5 | 9.8 | 0.0 | 9.8 | Mass % |

TABLE 3-continued

| Stream No | 1 | 3 | 4 | 2 | |
|---|---|---|---|---|---|
| $CO_2$ | 6.1 | 42.6 | 2.8 | 42.6 | Mass % |
| Methanol | 0.0 | 0.0 | 31.0 | 0.0 | Mass % |
| Dimethyl-ether | 0.0 | 36.3 | 49.7 | 36.4 | Mass % |
| Water | 0.0 | 0.0 | 16.5 | 0.0 | Mass % |

Purge gas stream 2 was recuperated by washing with a methanol stream 7 from methanol distillation column by introducing stream 2 (0.88 Nm³/h) at a pressure of 40 bar into the bottom of the purge washing unit (purge wash) and washing the stream with methanol in stream 7 being introduced at the top of the unit at a rate of 0.87 kg/h and a temperature of +14° C. From the bottom of the purge washing unit, a washed stream 8 was withdrawn at a rate of 1.05 kg/h. Composition of the above streams as analyzed is summarized in Table 4 below:

TABLE 4

| Stream No | 1 | 3 | 4 | |
|---|---|---|---|---|
| Flow | 0.88 | 0.62 | 0.71 | Nm³/h |
| $H_2$ | 11.3 | 0.0 | 0.0 | mass % |
| CO | 9.8 | 0.0 | 0.0 | mass % |
| $CO_2$ | 42.6 | 0.0 | 0.0 | mass % |
| Methanol | 0.0 | 96.2 | 81.0 | mass % |
| Dimethyl-ether | 36.4 | 0.0 | 17.5 | mass % |
| Water | 0.0 | 1.8 | 1.5 | mass % |

Stream 8 was then introduced at a flow of 1.05 kg/h and a pressure of 13 bar in a feed gas preheater (not shown) and preheated to 280° C.

The preheated stream 8 was passed to methanol dehydration reactor (MTD). In the MTD reactor methanol contained in the stream was dehydrated by contact with a fixed bed of a dehydration catalyst operated under substantially adiabatic conditions and a dehydrated product stream 9 was withdrawn from the reactor with a composition of 17.4 mole % methanol, 46.2 mole % DME and 36.2 mole % $H_2O$.

Product stream 9 was combined with top product stream 5 from the DME distillation column (DME column) in which DME contained in liquid process phase stream 4 was distilled off.

At conventional distillation conditions stream 4 (0.67 $Nm^3h$) of pure DME were recovered and withdrawn in stream 5 from the DME distillation column. Stream 5 was combined with stream 9 to 2.43 kg/h of a final product stream 10 consisting of fuel grade DME with a composition of DME, methanol and water as shown in Table 5 below:

TABLE 5

| Stream No | 5 | 9 | 10 | |
|---|---|---|---|---|
| Flow | 0.67 | 0.71 | 1.38 | $Nm^3/h$ |
| Methanol | 0.0 | 16.7 | 7.3 | Mass % |
| Dimethyl-ether | 100.0 | 63.7 | 84.2 | Mass % |
| Water | 0.0 | 19.6 | 8.5 | Mass % |

As apparent from Table 5, the composition of product stream 10 complies with the specification of fuel grade DME for utilization as fuel in compression ignition engines without further treatment of the product.

COMPARISON EXAMPLE

In a pilot plant process similar to that of the above Example a DME product was prepared with the exception of methanol washed stream 8 from the purge washing unit was not subject dehydration treatment.

In this process, stream 8 was directly combined with stream 5 from the DME distillation column as shown in FIG. 1 by dotted lines leaving a DME product stream 10A with a composition shown in Table 6 below:

TABLE 6

| Stream No | 1 | 3 | 4 | |
|---|---|---|---|---|
| Flow | 0.67 | 0.71 | 1.38 | $Nm^3/h$ |
| Methanol | 0.0 | 81.0 | 35.2 | Mass % |
| Dimethyl-ether | 100.0 | 17.5 | 64.1 | Mass % |
| Water | 0.0 | 1.5 | 0.6 | Mass % |

The composition of the DME product obtained in the Comparison Example has a concentration of methanol outside the allowable range for use of the product in compression ignition engines.

We claim:

1. A process for the preparation of a dimethyl ether product containing up to 20% by mass methanol and up to 20% by mass water being efficient as fuel in compression ignition engines from a hydrogen and carbon oxides containing synthesis gas, wherein the synthesis gas is converted to a mixed process gas of dimethyl ether, methanol and water in one or more catalytic reactors in the presence of a catalyst having activity both in synthesis of methanol and methanol dehydration;

the mixed process gas is cooled to obtain a liquid process phase (4) containing the produced methanol, dimethyl ether and water and a gaseous process phase (2A) containing unconverted synthesis gas and a part of produced dimethyl ether, which process comprises further steps of separating the gaseous phase and liquid phase;

passing the liquid phase to a first distillation unit (DME column) and distilling off a top product stream (5) containing dimethyl ether and methanol and withdrawing a bottom stream (6) containing methanol and water;

passing the bottom stream to a second distillation unit (MeOH column) and distilling off a methanol containing stream (7), introducing the methanol containing stream into a purge washing unit;

washing the gaseous process phase coming from the separating step with the methanol in a purge washing unit and withdrawing from the unit a washing stream of dimethyl ether and methanol (8);

converting a part of the methanol in the washing stream to dimethyl ether and water in a catalytic dehydration reaction (MTD) by contact with a dehydration catalyst;

withdrawing and cooling from the dehydration reactor a product stream (9) of dimethyl ether, water and unconverted methanol; and combining the top product stream from the first distillation unit with the cooled product stream from the dehydration reactor to obtain a combined product stream (10) of fuel grade dimethyl ether.

2. The process of claim 1, wherein a part of the gaseous process phase is recycled to the catalytic reactors.

3. The process of claim 1, wherein the combined product stream of fuel grade dimethyl ether comprises up to about 20% by weight methanol, up to about 20% by weight water, and greater than or equal to about 60% by weight of dimethyl ether.

4. A fuel grade dimethyl ether formed by the process of claim 1.

* * * * *